(12) United States Patent
Dubson et al.

(10) Patent No.: US 7,794,219 B2
(45) Date of Patent: Sep. 14, 2010

(54) PORTABLE ELECTROSPINNING DEVICE (75) Inventors: Alexander Dubson, Hadera (IL); Eli Bar, Moshav Megadim (IL)

(73) Assignee: Nicast Ltd., Lod (IL)

( * ) Notice: Subject to any disclaimer, the term of this patent is extended or adjusted under 35 U.S.C. 154(b) by 2097 days.

(21) Appl. No.: 10/471,278

(22) PCT Filed: Mar. 19, 2002

(86) PCT No.: PCT/IL02/00220

§ 371 (c)(1),
(2), (4) Date: Sep. 17, 2003

(87) PCT Pub. No.: WO02/074191

PCT Pub. Date: Sep. 26, 2002

(65) Prior Publication Data

US 2004/0094873 A1   May 20, 2004

(51) Int. Cl.
*B28B 1/00*   (2006.01)

(52) U.S. Cl. .................. 425/3; 425/7; 602/43
(58) Field of Classification Search ............ 602/41–56; 425/174.8 E, 3, 75
See application file for complete search history.

(56) References Cited

U.S. PATENT DOCUMENTS

| | | | |
|---|---|---|---|
| 2,491,889 A | 12/1949 | Bennett et al. | |
| 3,280,229 A | 10/1966 | Simons | |
| 3,425,418 A | 2/1969 | Chvapil et al. | |
| 3,625,745 A | 12/1971 | Wright et al. | |
| 3,688,317 A | 9/1972 | Kurtz | |
| 3,860,369 A | * 1/1975 | Brethauer et al. | ............... 425/3 |
| 4,009,508 A | * 3/1977 | Sternberg | ...................... 19/299 |
| 4,044,404 A | 8/1977 | Martin et al. | |
| 4,148,595 A | * 4/1979 | Bednarz | ....................... 425/75 |
| 4,159,640 A | 7/1979 | Lévêque et al. | |
| 4,223,101 A | 9/1980 | Fine et al. | |
| 4,323,525 A | 4/1982 | Bornat | |
| 4,345,414 A | 8/1982 | Bornat et al. | |
| 4,368,277 A | 1/1983 | Burinsky et al. | |
| 4,475,972 A | 10/1984 | Wong | |
| 4,524,036 A | 6/1985 | Gilding et al. | |
| 4,657,793 A | 4/1987 | Fisher | |
| 4,689,186 A | 8/1987 | Bornat | |
| 4,731,073 A | 3/1988 | Robinson | |
| 4,738,740 A | 4/1988 | Pinchuk et al. | |
| 4,739,013 A | 4/1988 | Pinchuk | |
| 4,743,252 A | 5/1988 | Martin, Jr. et al. | |
| 4,759,757 A | 7/1988 | Pinchuk | |

(Continued)

FOREIGN PATENT DOCUMENTS

EP   0009941   4/1980

(Continued)

*Primary Examiner*—Michael A. Brown
(74) *Attorney, Agent, or Firm*—Browdy and Neimark, P.L.L.C.

(57) ABSTRACT

An electrospinning device for generating a coat from a liquefied polymer, the device comprising: (a) a dispenser for dispensing the liquefied polymer; (b) a cavity having a longitudinal axis, comprising a first system of electrodes; the dispenser and the first system of electrodes being constructed and design such that the liquefied polymer is dispensed from the dispenser and forms a plurality of polymer fibers moving along the longitudinal axis; and (c) a mechanism for relocating the polymer fibers out of the cavity, in a direction of an object, so as to generate a coat on the object.

26 Claims, 3 Drawing Sheets

U.S. PATENT DOCUMENTS

| | | | |
|---|---|---|---|
| 4,769,030 A | 9/1988 | Pinchuk | |
| 4,798,606 A | 1/1989 | Pinchuk | |
| 4,802,145 A | 1/1989 | Mount, II | |
| 4,842,505 A | 6/1989 | Annis et al. | |
| 4,872,455 A | 10/1989 | Pinchuk et al. | |
| 4,878,908 A | 11/1989 | Martin et al. | |
| 4,880,002 A | 11/1989 | MacGregor | |
| 4,904,174 A * | 2/1990 | Moosmayer et al. | .. 425/174.8 E |
| 4,905,367 A | 3/1990 | Pinchuk et al. | |
| 4,965,110 A | 10/1990 | Berry | |
| 4,990,158 A | 2/1991 | Kaplan et al. | |
| 4,997,600 A | 3/1991 | Okumura et al. | |
| 5,019,090 A | 5/1991 | Pinchuk | |
| 5,024,671 A | 6/1991 | Tu et al. | |
| 5,024,789 A | 6/1991 | Berry | |
| 5,084,065 A | 1/1992 | Weldon et al. | |
| 5,092,877 A | 3/1992 | Pinchuk | |
| 5,116,360 A | 5/1992 | Pinchuk et al. | |
| 5,133,742 A | 7/1992 | Pinchuk | |
| 5,147,725 A | 9/1992 | Pinchuk | |
| 5,226,913 A | 7/1993 | Pinchuk | |
| 5,298,255 A | 3/1994 | Sawamoto et al. | |
| 5,334,201 A | 8/1994 | Cowan | |
| 5,360,397 A | 11/1994 | Pinchuk | |
| 5,376,117 A | 12/1994 | Pinchuk et al. | |
| 5,383,922 A | 1/1995 | Zipes et al. | |
| 5,383,928 A | 1/1995 | Scott et al. | |
| 5,415,664 A | 5/1995 | Pinchuk | |
| 5,419,760 A | 5/1995 | Narciso, Jr. | |
| 5,545,208 A | 8/1996 | Wolff et al. | |
| 5,549,663 A | 8/1996 | Cottone, Jr. | |
| 5,554,722 A | 9/1996 | Eichenauer et al. | |
| 5,558,809 A | 9/1996 | Groh et al. | |
| 5,575,818 A | 11/1996 | Pinchuk | |
| 5,591,227 A | 1/1997 | Dinh et al. | |
| 5,609,629 A | 3/1997 | Fearnot et al. | |
| 5,624,411 A | 4/1997 | Tuch | |
| 5,627,368 A | 5/1997 | Moake | |
| 5,628,788 A | 5/1997 | Pinchuk | |
| 5,632,772 A | 5/1997 | Alcime et al. | |
| 5,637,113 A | 6/1997 | Tartaglia et al. | |
| 5,639,278 A | 6/1997 | Dereume et al. | |
| 5,653,747 A | 8/1997 | Dereume | |
| 5,697,967 A | 12/1997 | Dinh et al. | |
| 5,700,269 A | 12/1997 | Pinchuk et al. | |
| 5,723,004 A | 3/1998 | Dereume et al. | |
| 5,725,567 A | 3/1998 | Wolff et al. | |
| 5,726,107 A | 3/1998 | Dahringer et al. | |
| 5,733,327 A | 3/1998 | Igaki et al. | |
| 5,741,333 A | 4/1998 | Frid | |
| 5,749,921 A | 5/1998 | Lenker et al. | |
| 5,755,722 A | 5/1998 | Barry et al. | |
| 5,755,774 A | 5/1998 | Pinchuk | |
| 5,755,778 A | 5/1998 | Kleshinski | |
| 5,766,710 A | 6/1998 | Turnlund et al. | |
| 5,797,887 A | 8/1998 | Rosen et al. | |
| 5,824,048 A | 10/1998 | Tuch | |
| 5,824,049 A | 10/1998 | Ragheb et al. | |
| 5,837,008 A | 11/1998 | Berg et al. | |
| 5,843,172 A | 12/1998 | Yan | |
| 5,849,037 A | 12/1998 | Frid | |
| 5,855,598 A | 1/1999 | Pinchuk | |
| 5,871,538 A | 2/1999 | Dereume | |
| 5,900,246 A | 5/1999 | Lambert | |
| 5,928,247 A | 7/1999 | Barry et al. | |
| 5,938,697 A | 8/1999 | Killion et al. | |
| 5,948,018 A | 9/1999 | Dereume et al. | |
| 5,968,070 A | 10/1999 | Bley et al. | |
| 5,968,091 A | 10/1999 | Pinchuk et al. | |
| 5,980,551 A | 11/1999 | Summers et al. | |
| 5,980,972 A | 11/1999 | Ding | |
| 6,001,125 A | 12/1999 | Golds et al. | |
| 6,004,346 A | 12/1999 | Wolff et al. | |
| 6,013,099 A | 1/2000 | Dinh et al. | |
| 6,017,362 A | 1/2000 | Lau | |
| 6,019,788 A | 2/2000 | Butters et al. | |
| 6,019,789 A | 2/2000 | Dinh et al. | |
| 6,023,170 A | 2/2000 | Hilhorst et al. | |
| 6,102,939 A | 8/2000 | Pinchuk | |
| 6,106,913 A | 8/2000 | Scardino et al. | |
| 6,117,425 A | 9/2000 | MacPhee et al. | |
| 6,165,212 A | 12/2000 | Dereume et al. | |
| 6,252,129 B1 | 6/2001 | Coffee | |
| 6,265,333 B1 | 7/2001 | Dzenis et al. | |
| 6,270,793 B1 | 7/2001 | Van Dyke et al. | |
| 6,306,424 B1 | 10/2001 | Vyakarnam et al. | |
| 6,308,509 B1 | 10/2001 | Scardino et al. | |
| 6,309,413 B1 | 10/2001 | Dereume et al. | |
| 6,604,925 B1 | 8/2003 | Dubson | |
| 2001/0020652 A1 | 9/2001 | Kadlubowski et al. | |
| 2002/0002395 A1 | 3/2002 | Berg et al. | |
| 2002/0081732 A1 | 6/2002 | Bowlin et al. | |
| 2002/0090725 A1 | 7/2002 | Simpson et al. | |
| 2003/0171053 A1 | 9/2003 | Sanders | |

FOREIGN PATENT DOCUMENTS

| | | |
|---|---|---|
| EP | 0223374 | 5/1987 |
| EP | 0253539 | 1/1988 |
| EP | 0266035 | 5/1988 |
| EP | 0523960 | 1/1993 |
| GB | 2142870 | 1/1985 |
| JP | 161563 | 7/1991 |
| WO | WO 01/54667 | 2/2001 |
| WO | WO 01/66035 | 9/2001 |
| WO | WO 02/40242 | 5/2002 |
| WO | WO 02/49535 | 6/2002 |
| WO | WO 02/49536 | 6/2002 |
| WO | WO 02/49678 | 6/2002 |
| WO | WO 02/074189 | 9/2002 |
| WO | WO 02/074190 | 9/2002 |

* cited by examiner

PORTABLE ELECTROSPINNING DEVICE

RELATED PATENT APPLICATION

This application is a National Phase Application of PCT/IL02/00220 International Filing Date 19 Mar. 2002, which claims priority from. U.S. patent application Ser. No. 09/982,017 filed 19 Oct. 2001, which claims priority from U.S. Provisional Patent Application No. 60/276,956 filed 20 Mar. 2001.

FIELD AND BACKGROUND OF THE INVENTION

The present invention relates to an electrospinning device and, more particularly, to a portable electrospinning device useful in providing a coat onto a verity of objects, such as wounds and the like.

Skin dressing materials used for covering skin defects are required, in general, to have skin compatibility, low or no skin irritation characteristics and sufficiently flexibility, so as to expand as the skin there underneath moves. In addition, it is desired that such skin dressing materials will serve as a barrier against infection agents, such as bacteria, so as to prevent infections.

When a skin defect is characterized by a large area of skin loss, such as in the case of a burn, the defect region is first treated by being covered with a conventional wound dressing material, as a first aid, and then via grafting of skin from other parts of the body.

Known in the art are wound dressings consisting of a thin flexible material, having an adhesive on one side, which are applied to an open wound of a patient following medical treatment of the wound. The flexible nature of the material permits the dressing to conform to virtually any contour of the patient at the location where the dressing is applied.

Typical wound dressings, however, are often applied to the patient during or after stretching of the dressing. Such stretching is known to cause discomfort to the patient and irritation to the area surrounding the wound. Moreover, on weak or damaged skin, as in the elderly, the stretching forces can cause serious skin damage. Furthermore, the flexibility of conventional skin dressing materials comes into question because these materials, once stretched, do not flexibly deform enough following the movement of the skin, which sometimes causes discomfort and/or pain.

The process of application of the wound dressing onto a wounded site often requires contact between fingers and the surface of the material during application, which contact may contaminate the surface adjacent to the wound beneath the dressing. Hence, maintaining the sterility of the dressing during the application process is an important consideration when designing a wound dressing.

It is recognized that the healing of a wound occurs as the epithelium migrates by growth generally from the periphery inward. Therefore, care is taken not to damage unnecessarily or to irritate this new area of growth or existing compromised tissue.

Many local treatments of cuts, wounds, burns and the like require some kind of pharmaceutical agent to be applied on the damaged site, prior to the application of a wound dressing. The advantages gained by local therapy include high concentrations of the drug at the actual site of injury. However, since in these treatments the medication is dispensed over an open wound, the wound dressing need to be stripped off before treating the wound.

Frequently, with prior art dressings, problems can occur during dressing changes, e.g. when the dressing adheres to the epithelium. In these instances, there is a risk that removal of the dressing will damage the sensitive tissue and new growth, thereby causing a regression in the progress of wound healing.

Considering the various types of wounds, the numerous dressings that are presently available, and the various stages of healing, there remains a need for a substantially sterile dressing that minimizes damages to the injured site, both during the application and during the removal of the dressings.

The present invention provides solutions to the problems associated with prior art wound dressing techniques.

SUMMARY OF THE INVENTION

According to one aspect of the present invention there is provided an electrospinning device for generating a coat from a liquefied polymer, the device comprising: (a) a dispenser for dispensing the liquefied polymer; (b) a cavity having a longitudinal axis, comprising a first system of electrodes; the dispenser and the first system of electrodes being constructed and design such that the liquefied polymer is dispensed from the dispenser and forms a plurality of polymer fibers moving along the longitudinal axis; and (c) a mechanism for relocating the polymer fibers out of the cavity, in a direction of an object, so as to generate a coat on the object.

According to further features in preferred embodiments of the invention described below, the mechanism comprises at least one blower, positioned adjacent to the dispenser, and generating an airflow substantially directed along the longitudinal axis.

According to still further features in the described preferred embodiments the electrospinning device further comprising a first reservoir for holding the liquefied polymer.

According to still further features in the described preferred embodiments the electrospinning device further comprising a second reservoir for holding a pharmaceutical agent to be mixed with the liquefied polymer.

According to another aspect of the present invention there is provided a method of generating a coat from a liquefied polymer, the method comprising dispensing the liquefied polymer within a first electric field present in a cavity having a longitudinal axis, thereby providing a plurality of polymer fibers moving along the longitudinal axis, and relocating the polymer fibers out of the cavity, in a direction of an object so as to generate a coat onto the object.

According to further features in preferred embodiments of the invention described below, the method further comprising incorporating at least one drug within the liquefied polymer, for delivery of the at least one drug into a vasculature of the organism, during or after generating the coat.

According to yet another aspect of the present invention there is provided a nonwoven sterile wound dressing comprising at least one layer of polymer fibers shaped in accordance with an individual wound and body geometry, the nonwoven wound dressing having at least one characteristic selected from the group consisting of: (a) having a predetermined porosity; (b) flexible in accordance with a motion of the individual; (c) removable when placed under a sufficient amount of liquid; and (d) having at least one drug incorporated therein, for delivery of the at least one drug into the body vasculature during or after application of the wound dressing.

According to still another aspect of the present invention there is provided a nonwoven sterile wound dressing comprising at least one layer of polymer fibers shaped in accordance with an individual wound and body geometry, the nonwoven wound dressing having at least two characteristics selected from the group consisting of: (a) having a predetermined porosity; (b) flexible in accordance with a motion of the individual; (c) removable when placed under a sufficient amount of liquid; and (d) having at least one drug incorporated therein, for delivery of the at least one drug into the body vasculature during or after application of the wound dressing.

According to an additional aspect of the present invention there is provided a nonwoven sterile wound dressing comprising at least one layer of polymer fibers shaped in accordance with an individual wound and body geometry, the nonwoven wound dressing having at least three characteristics selected from the group consisting of: (a) having a predetermined porosity; (b) flexible in accordance with a motion of the individual; (c) removable when placed under a sufficient amount of liquid; and (d) having at least one drug incorporated therein, for delivery of the at least one drug into the body vasculature during or after application of the wound dressing.

According to yet an additional aspect of the present invention there is provided a nonwoven sterile wound dressing comprising at least one layer of polymer fibers shaped in accordance with an individual wound and body geometry, the nonwoven wound dressing: (a) having a predetermined porosity; (b) flexible in accordance with a motion of the individual; (c) removable when placed under a sufficient amount of liquid; and (d) having at least one drug incorporated therein, for delivery of the at least one drug into the body vasculature during or after application of the wound dressing.

According to further features in preferred embodiments of the invention described below, the nonwoven sterile wound dressing is an artificial skin.

According to still further features in the described preferred embodiments the polymer fibers are biocompatible.

According to still further features in the described preferred embodiments the polymer fibers are selected from the group consisting of biodegradable polymer fibers and biostable polymer fibers.

According to still an additional aspect of the present invention there is provided a method of connecting two vessels having open ends, the method comprising, attaching the two open ends of the two vessels and, via electrospinning, providing a coat onto at least a portion of the two vessels so as to adhere the two open ends.

According to further features in preferred embodiments of the invention described below, providing a coat comprises dispensing a liquefied polymer within a first electric field present in a cavity having a longitudinal axis, thereby providing a plurality of polymer fibers moving along the longitudinal axis, and relocating the polymer fibers out of the cavity, in a direction of the at least a portion of the two vessels.

According to still further features in the described preferred embodiments the method further comprising incorporating at least one drug within the liquefied polymer, for delivery of the at least one drug into at least one vessel during or after providing the coat.

According to a further aspect of the present invention there is provided a method of recording a fingerprint of an individual having a finger, the method comprising: via electrospinning, coating the finger by a nonwoven material; and removing the nonwoven material from the finger so as to produce data information representative of the fingerprint of the finger.

According to further features in preferred embodiments of the invention described below, coating comprises dispensing a liquefied polymer within a first electric field present in a cavity having a longitudinal axis, thereby providing a plurality of the polymer fibers moving along the longitudinal axis, and relocating the polymer fibers out of the cavity, in a direction of the finger so as to generate a coat onto the finger.

According to yet a further aspect of the present invention there is provided a method of adhering two objects having contact surfaces, the method comprising: via electrospinning, coating at least one contact surface by a nonwoven material; and attaching the contact surfaces together hence adhering the two objects.

According to further features in preferred embodiments of the invention described below, the nonwoven material is made from polymer fibers.

According to still further features in the described preferred embodiments coating comprises dispensing a liquefied polymer within a first electric field present in a cavity having a longitudinal axis, thereby providing a plurality of the polymer fibers moving along the longitudinal axis, and relocating the polymer fibers out of the cavity, in a direction of the at least one contact surface.

According to yet a further aspect of the present invention there is provided a method of wound dressing by electrospinning, the method comprising dispensing a liquefied polymer within a first electric field present in a cavity having a longitudinal axis, thereby providing a plurality of polymer fibers moving along the longitudinal axis, and relocating the polymer fibers out of the cavity, in a direction of an object so as to generate a wound dressing onto the object.

According to further features in preferred embodiments of the invention described below, the relocating is done by airflow.

According to still further features in the described preferred embodiments the object is a portion of a body of an organism.

According to still further features in the described preferred embodiments the object is a skin of an organism.

According to still further features in the described preferred embodiments the object is a wounded skin of an organism.

According to still further features in the described preferred embodiments the portion is selected from the group consisting of an internal portion and an external portion of the organism.

According to still further features in the described preferred embodiments the object is a blood vessel.

According to still further features in the described preferred embodiments the object is selected from the group consisting of an artery and a vein.

According to still further features in the described preferred embodiments the object is a rotating mandrel.

According to still further features in the described preferred embodiments the dispensing is done by a dispenser.

According to still further features in the described preferred embodiments the dispenser comprises a mechanism for forming a jet of the liquefied polymer.

According to still further features in the described preferred embodiments the mechanism for forming a jet of the liquefied polymer includes a dispensing-electrode.

According to still further features in the described preferred embodiments the first electric field is generated by the dispensing electrode and by a first system of electrodes.

According to still further features in the described preferred embodiments the first system of electrodes comprises a circular electrode being at a first potential relative to the dispenser, and spaced apart from the dispenser, along the longitudinal axis.

According to still further features in the described preferred embodiments the method further comprising intertwining at least a portion of the plurality of polymer fibers, so as to provide at least one polymer fiber bundle moving along the longitudinal axis.

According to still further features in the described preferred embodiments the intertwining is done by a second system of electrodes, being laterally displaced from the dispenser, being at a second potential relative to the dispenser and capable of providing a second electric field having at least one rotating component about the longitudinal axis.

According to still further features in the described preferred embodiments the second system of electrodes includes at least one rotating electrode, operable to rotate about the longitudinal axis.

According to still further features in the described preferred embodiments the cavity is designed such that the airflow velocity increases as a function of a distance from the dispenser along the longitudinal axis.

According to still further features in the described preferred embodiments the cavity is characterized by a gradually decreases cross-sectional area along a direction of motion of the polymer fibers.

According to still further features in the described preferred embodiments the cavity comprises a perforated plate positioned at a first terminal of the cavity.

According to still further features in the described preferred embodiments the cavity is opened at a second terminal of the cavity.

According to still further features in the described preferred embodiments the method further comprising incorporating at least one drug within the liquefied polymer, for delivery of the at least one drug into the vessel during or after generating the coat.

According to still further features in the described preferred embodiments the liquefied polymer is biocompatible.

According to still further features in the described preferred embodiments the liquefied polymer is selected from the group consisting of a biodegradable liquefied polymer and a biostable liquefied polymer.

The present invention successfully addresses the shortcomings of the presently known configurations by providing a method and apparatus for providing a nonwoven coat far exceeding prior art.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of an electrospinning device which can be used for generating a coat from a liquefied polymer. Specifically, the present invention can be used to provide first aid for wounds, burns, cuts and the like, and to fabricate artificial skin. Additionally, the present invention can be used to record fingerprints, to connect any two objects such as blood vessels, and to provide a coat to various objects having composite shapes.

Figure 1:
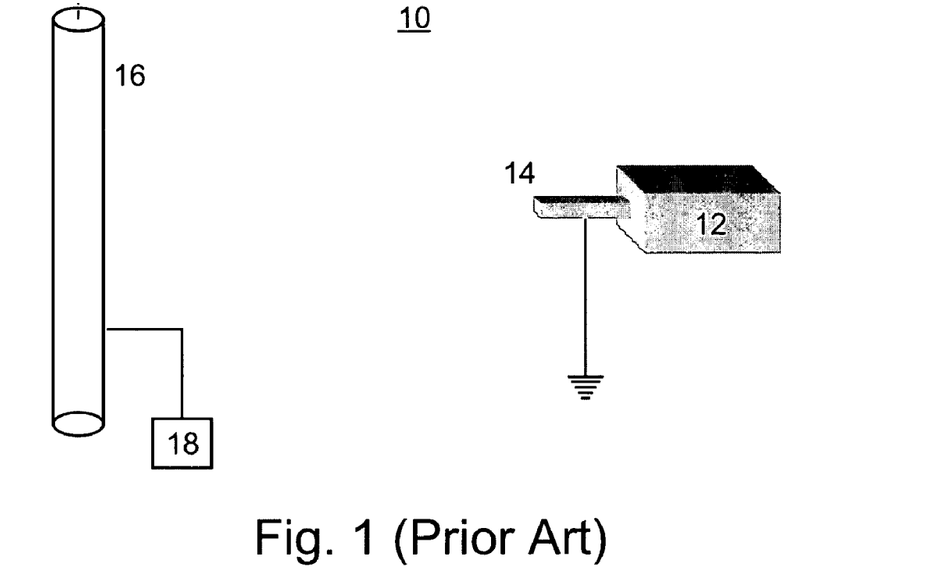
FIG. 1 is a schematic illustration of a prior art electrospinning apparatus.

For purposes of better understanding the present invention, as illustrated in FIGS. 2-5 of the drawings, reference is first made to the construction and operation of a conventional (i.e., prior art) electrospinning apparatus as illustrated in FIG. 1.

FIG. 1 illustrates an apparatus for manufacturing a nonwoven material using a conventional electrospinning apparatus, which is referred to herein as apparatus 10.

Apparatus 10 includes a dispenser 12 which can be, for example, a bath provided with one or more capillary apertures 14. Dispenser 12 serves for storing the polymer to be spun in a liquid form, i.e., dissolved or melted. Dispenser 12 is positioned at a predetermined distance from a precipitation electrode 16. Precipitation electrode 16 serves for forming a structure thereupon. Precipitation electrode 16 is typically manufactured in accordance with the geometrical properties of the final product which is to be fabricated.

Dispenser 12 is typically grounded, while precipitation electrode 16 is connected to a source of high voltage, preferably of negative polarity, thus forming an electric field between dispenser 12 and precipitation electrode 16. Alternatively, as shown in FIG. 1, precipitation electrode 16 can be grounded while dispenser 12 is connected to a source 18 of high voltage with positive polarity.

To generate a nonwoven material, a liquefied polymer (e.g., melted polymer or dissolved polymer) is extruded, for example under the action of hydrostatic pressure, or using a pump (not shown in FIG. 1), through capillary apertures 14 of dispenser 12. As soon as meniscus of the extruded liquefied polymer forms, a process of solvent evaporation or cooling starts, which is accompanied by the creation of capsules with a semi-rigid envelope or crust. An electric field, occasionally accompanied by a unipolar corona discharge in the area of dispenser 12, is generated by the potential difference between dispenser 12 and precipitation electrode 16. Because the liquefied polymer possesses a certain degree of electrical conductivity, the above-described capsules become charged. Electric forces of repulsion within the capsules lead to a drastic increase in hydrostatic pressure. The semi-rigid envelopes are stretched, and a number of point micro-ruptures are formed on the surface of each envelope leading to spraying of ultra-thin jets of liquefied polymer from dispenser 12.

Under the effect of a Coulomb force, the jets depart from dispenser 12 and travel towards the opposite polarity electrode, i.e., precipitation electrode 16. Moving with high velocity in the inter-electrode space, the jet cools or solvent therein evaporates, thus forming fibers which are collected on the surface of precipitation electrode 16.

When using precipitation electrodes characterized by sharp edges and/or variously shaped and sized recesses, the electric field magnitude in the vicinity of precipitation electrode 16 may exceed the air electric strength (about 30 kV/cm), and a corona discharge may develop in the area of precipitation electrode 16. The effect of corona discharge decreases the coating efficiency of the process as described hereinbelow, and may even resultant in a total inability of fibers to be collected upon precipitation electrode 16.

Corona discharge initiation is accompanied by the generation of a considerable amount of air ions having opposite charge sign with respect to the charged fibers. Since an electric force is directed with respect to the polarity of charges on which it acts, theses ions start to move at the opposite direction to fibers motion i.e., from precipitation electrode 16 towards dispenser 12. Consequently, a portion of these ions generate a volume charge (ion cloud), non-uniformly distributed in the inter-electrode space, thereby causing electric field lines to partially close on the volume charge rather than on precipitation electrode 16. Moreover, the existence of an opposite volume charge in the inter-electrode space, decreases the electric force on the fibers, thus resulting in a large amount of fibers accumulating in the inter-electrode space and gradually settling under gravity force. It will be appreciated that such an effect leads to a low-efficiency process of fiber coating.

Using a large radius cylinder or a substantially flat plane as a precipitation electrode may diminish the effect described above. However, this effect is severe and limiting when complicated precipitation electrodes are employed for fabricating intricate-profile structures. Moreover, apparatus 10 is typically designed for manufacturing a nonwoven material having a predetermined structure, or for coating an object which is mounted on a rotating mandrel.

It is recognized that such requirements limit the number of possible applications for which apparatus 10 can be employed. For example, apparatus 10 cannot be used for coating objects which are too large or too complicated for being mounted on a rotating mandrel, or for coating a portion of a blood vessel during surgery.

In a conventional electrospinning process as described hereinabove the precipitation is done within a substantially high electric field, thus the process may only be employed for coating objects which may be positioned under high voltage. Furthermore, the presence of electric field near precipitation electrode 16 prevents fibers from penetrating into narrow openings, inclined shapes, etc. whenever such structures exist in precipitation electrode 16.

While reducing the present invention to practice, it was uncovered that the above limitations can be overcome by a providing a substantial drop of the electric field strength in the vicinity of the object to be coated by the fibers.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
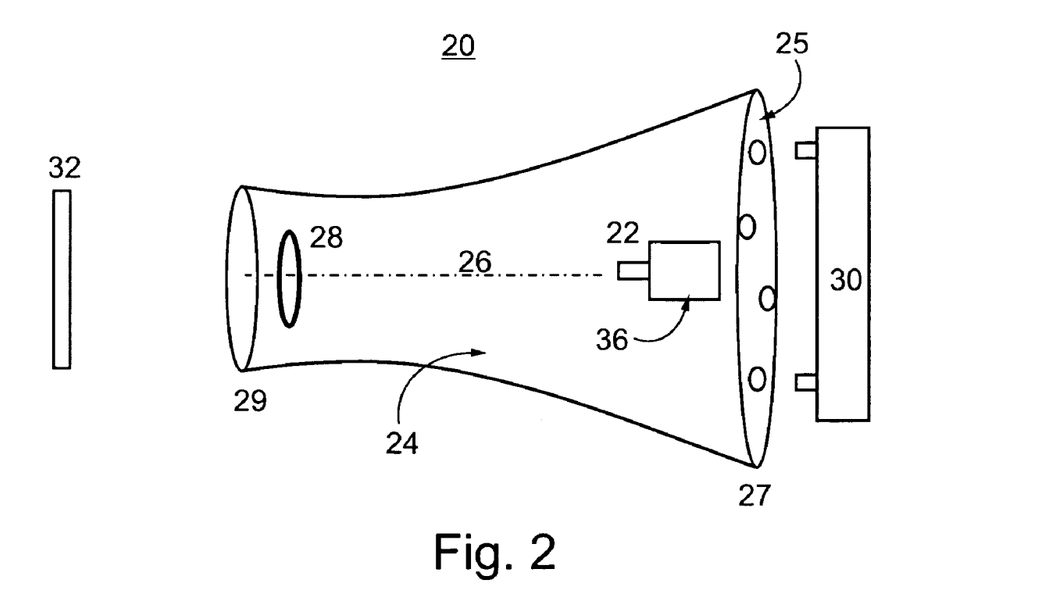
FIG. 2 is a schematic illustration of an electrospinning device for generating a coat from a liquefied polymer, according to the present invention.

Referring now again to the drawings, FIG. 2 illustrates an electrospinning device, generally referred to herein as device 20, for generating a coat from a liquefied polymer according to the teachings of the present invention. Device 20 includes a dispenser 22 for dispensing the liquefied polymer, and a cavity 24 having a longitudinal axis 26, and comprising a first system of electrodes 28. System of electrodes 28 may be, for example, a circular electrode.

According to a preferred embodiment of the present invention dispenser 22 and first system of electrodes 28 are constructed and design such that the liquefied polymer is dispensed from dispenser 22 and forms a plurality of polymer fibers moving along longitudinal axis 26, as detailed hereinabove with respect to apparatus 10. Hence dispenser 22 and system of electrodes 28 are kept under a potential difference generate an electric field therebetween.

Device 20 further includes a mechanism 30 for relocating the polymer fibers out of cavity 24, in a direction of an object 32, so as to generate a coat on object 32. Mechanism 30 may include, for example, at least one blower, positioned adjacent to dispenser 22. The blower is configured to generate an airflow substantially directed along longitudinal axis 26, to maintain the velocity of the polymer fiber while passing near system 28.

Cavity 24 preferably comprises a perforated plate 25 positioned at a first terminal 27 of cavity 24, so as to allow sufficient airflow from mechanism 30 which is preferably located outside cavity 24, behind dispenser 22. At a second terminal 29, near system of electrodes 28, cavity 24 is opened.

According to a preferred embodiment of the present invention cavity 24 is designed such that the airflow velocity increases as a function of a distance from dispenser 22 along longitudinal axis 26. A typical example for such design is a gradually decreased cross-sectional area of cavity 24 as a function of a distance from dispenser 22 along longitudinal axis 26.

In order to provide the desired electric field, dispenser 22 and system of electrodes 28 are kept under a potential difference. In accordance with a preferred electrostatic configuration of the invention, dispenser 22 is kept under a positive polarity potential and both system of electrodes 28 and object 32 are grounded, i.e., being at earth-zero potential. Such electrostatic configuration is intended to substantially diminish any remnant component of electric field between apparatus 20 and object 32.

According to a preferred embodiment of the present invention, dispenser 22 comprises a mechanism for forming a jet of the liquefied polymer, such as, but not limited to, a dispensing electrode, manufactured as a needle. Additionally, dispenser 22 may include a first reservoir 36 for holding the liquefied polymer. In operation mode of device 20, a jet of the liquefied polymer is dispensed by dispenser 22, and then, subjected to the electric field, moves through cavity 24, substantially along longitudinal axis 26. As described hereinabove, the jet cools or solvent therein evaporates, thus forming the polymer fibers. Beside the electrical forces present between the charged fibers and the electric field, additional mechanical forces, generated by mechanism 30, act on the polymer fibers concertedly with the electric forces.

Unlike a conventional electrospinning apparatus (e.g., apparatus 10), high air flow rate near system of electrodes 28, prevent fiber sedimentation on system of electrodes 28, although high attractive electric forces may be present between system of electrodes 28 and the polymer fibers. This phenomenon may be explained both by the mechanical forces directing the fibers outward of cavity 24 and by a presence of an air interlayer which serve for "lubricating" system of electrodes 28. For example, in a preferred embodiment in which system of electrodes 28 is a circular electrode (see FIG. 2), the airflow carries the polymer fibers through the circular electrode. In accordance with a preferred embodiment of the present invention, the velocity of the airflow generated by mechanism 30 increases due to the special geometry of cavity 24. Thus, the relocating effect of mechanism 30 is optimized by cavity 24.

Hence, device 20, which may be manufactured as a compact portable device, essentially serves as an electrostatic sprayer. Since outside the device the electric field is absent, orientation of fiber movement is maintained only by the mechanical forces due to airflow, which are sufficient for fiber relocation. Since air flow is known to have a decaying property, the velocity of the polymer fibers decreases as a function of a distance from device 20. Hence, the polymer fibers arrive to object 32, while moving with nearly zero velocity. Due to Coulomb forces present between the charged polymer fibers and the grounded object, the polymer fibers finally sediment on object 32.

It would be appreciated that the absence of electric field lines closing on object 32 ensures an enhanced coating process, in which the polymer fibers are able to penetrate even into relatively narrow openings. In addition the absence of counteracting volume charge near object 32, allows a very thin coating the thickness of which is typically of several micrometers.

Depending on the use of the nonwoven material formed by device 20, it may be required to enhance the strength and/or elasticity of the final product. This is especially important in medical applications, such as wound dressings, where a combination of high elasticity, strength, small thickness, porosity, and low basis weight are required.

According to a preferred embodiment of the present invention the strength of the nonwoven material may be significantly enhanced, by employing an additional electric field having at least one rotating element, as described hereinbelow.

Figure 3:
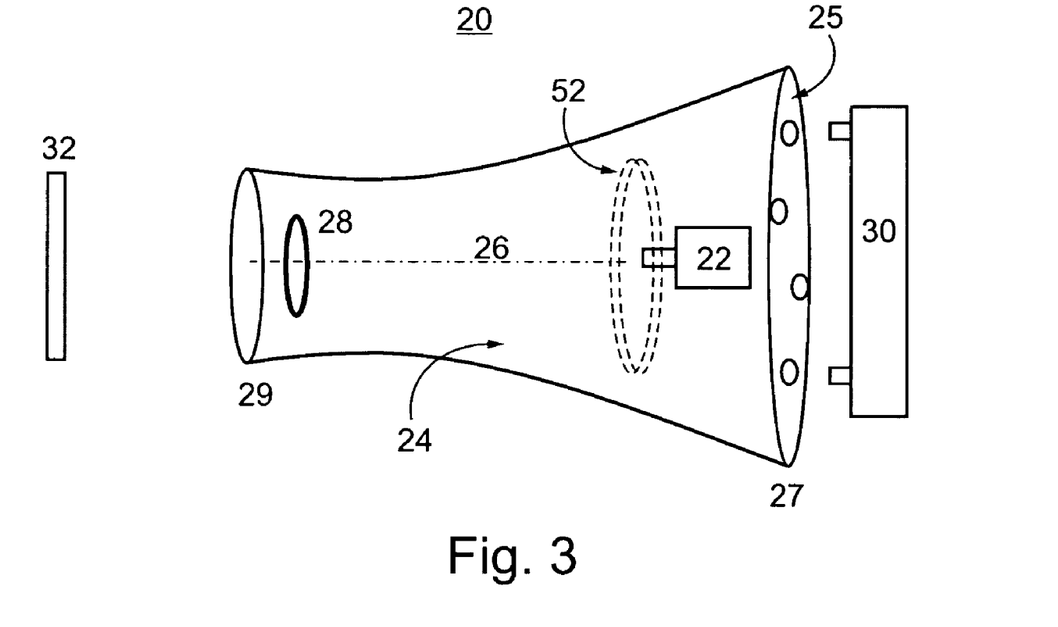
FIG. 3 is a is a schematic illustration of the electrospinning device further comprising a mechanism for intertwining at least a portion of the polymer fibers, according to the present invention.

Referring to FIG. 3, device 20 further includes a mechanism 52 for intertwining at least a portion of the polymer fibers, so as to provide at least one polymer fiber bundle moving in a direction system 28. Mechanism 52 may include any mechanical and/or electronic components which are capable for intertwining the polymer fibers "on the fly", as is further detailed hereinunder, with reference to FIGS. 4-5.

Figure 4:
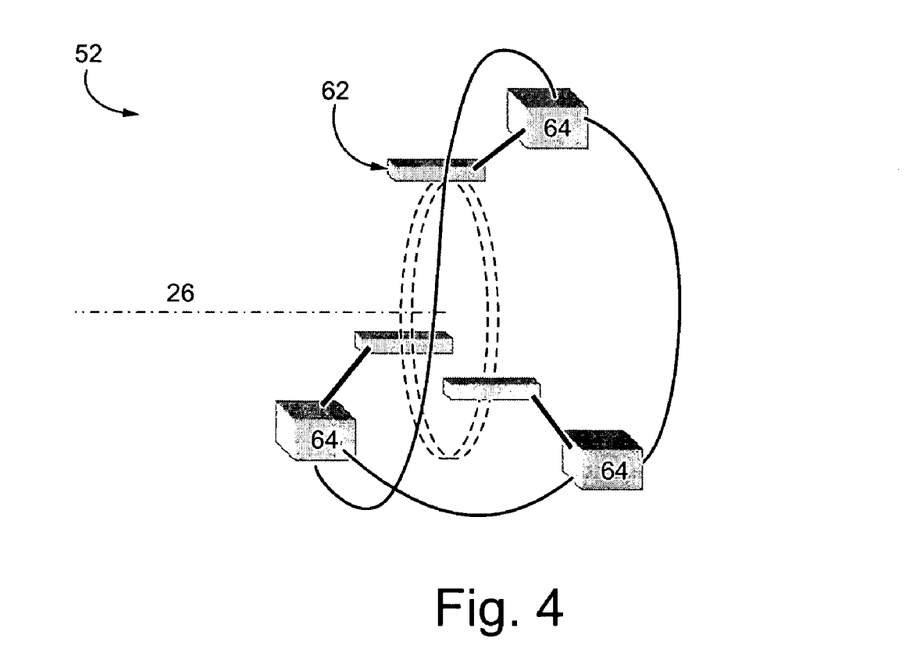
FIG. 4 is a schematic illustration of the intertwining mechanism in the form of a plurality of stationary electrodes, according to the present invention.

Thus, FIG. 4 illustrates one embodiment of the present invention in which mechanism 52 includes a second system of electrodes being laterally displaced from dispenser 22 and preferably at a second potential relative to dispenser 22. According to a preferred embodiment of the present invention the second system of electrodes may be constructed in any way known in the art for providing an electric field rotating around longitudinal axis 26.

For example, as shown in FIG. 4, the second system of electrodes may include two or more stationary electrodes 62, connected to at least one power source 64, so that the potential difference between electrodes 62 and system 28 (and between electrodes 62 and dispenser 22) varies in time. Power sources 64, being electronically communicating with each other so as to synchronize a relative phase between electrodes 62. Hence, each of stationary electrodes 62 generates a time-dependent electric field having a constant direction. The electronic communication between power sources 64 ensures that the sum of all (time-dependent) field vectors is rotating around longitudinal axis 26.

Figure 5:
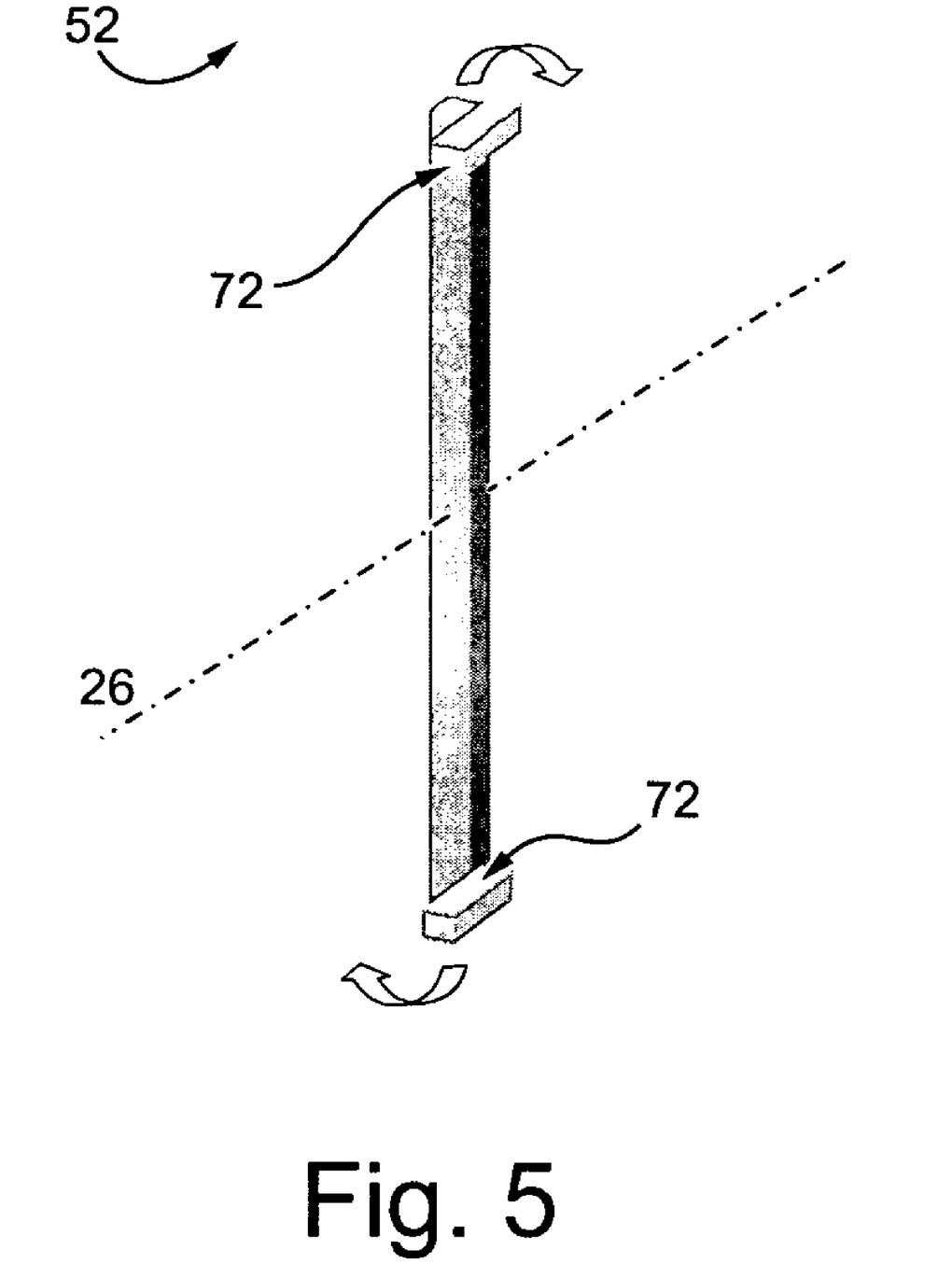
FIG. 5 is a schematic illustration of the intertwining mechanism in the form of at least one rotating electrodes, according to the present invention.

Reference is now made to FIG. 5, in which mechanism 52 is manufactured as at least one rotating electrode 72, operable to rotate around longitudinal axis 26. Rotating electrode 72, being at a second potential relative to dispenser 22, generates an electric field, the direction of which follows the motion of rotating electrode 72, hence an electric field having at least one rotating component is generated.

According to the presently preferred embodiment of the invention, in operation mode of device 20, the liquefied polymer is dispensed by dispenser 22, and then, subjected to the electric field, moves inside cavity 24. The electric field has at least one rotating component around longitudinal axis 26 (generated by the potential difference between mechanism 52 and system 28) and a stationary electric field (generated by the potential difference between dispenser 22 and system 28). Hence, in addition to the movement in the direction of system 28, the jets of liquefied polymer, under the effect of the rotating component of the electric field twist around longitudinal axis 26. The rotation frequency may be controlled by a suitable choice of configuration for the system of electrodes, as well as on the value of the potential differences employed.

At a given time, the effect of the rotating component of the electric field on the jets neighboring mechanism 52 is larger than the effect on the jets which are located far from mechanism 52. Hence, the trajectories of the fibers start crossing one another, resulting in physical contacts and entanglement between fibers prior to precipitation.

Thus, device 20 generates higher-order formations of fiber bundles from the elementary fibers in the spray jet. The structure of the formed fiber bundles is inhomogeneous and depends on the distance of the fiber bundle from mechanism 52. Specifically, the extent of fiber twisting and interweaving, and the amount of fibers in the bundle, is an increasing function of the distance from mechanism 52. During the motion of the bundles in cavity 24, they may also intertwine with one another, forming yet thicker bundles.

The bundles, while formed, move in cavity 24, directed to system of electrodes 28, and continue, due to the forces provided by mechanism 30, out of cavity 24 forming the nonwoven material onto object 32. The formed material has three-dimensional reticular structure, characterized by a large number of sliding contacts between fibers. Such contacts significantly increase the strength of the material, due to friction forces between fibers. The ability of fibers for mutual displacement increases the elasticity of the nonwoven material under loading.

Device 20 may provide enhanced coating onto numerous kinds of objects, for medical as well as for industrial purposes. According to a preferred embodiment of the present invention object 32 may be, for example, a portion of a body of an organism, such as but not limited to, a skin an artery and a vein. Thus the present invention can be used to provide a nonwoven coat onto both internal and external organs. Alternatively, object 32 may be a rotating mandrel having an intricate-profile structure.

In medical applications, the present invention can be used to provide wound dressing without the need to stretch the dressing, prior to or during application.

Thus, according to another aspect of the invention there is provided a method of wound dressing by electrospinning. The method comprises the following steps which may be executed, for example, using device 20. Hence, in a first step a liquefied polymer is dispensed within a first electric field present in a cavity having a longitudinal axis, thereby providing a plurality of polymer fibers moving along the longitudinal axis. In a second step, the polymer fibers are being relocated out of the cavity, in a direction of an object so as to generate a wound dressing thereupon.

According to a preferred embodiment of the present invention, the method may further comprise the step of intertwining at least a portion of the polymer fibers, so as to provide at least one polymer fiber bundle moving in the direction of the object.

The liquefied polymer may be chosen, as further detailed hereinunder, so as to allow maximal flexibility of the dressing. Moreover, since the process wound dressing (as employed, e.g., by device 20) requires no hand contact with the nonwoven material during application, the present invention successfully maintains the sterility of the dressing during the application process.

Some skin defects, such as burns and deep cuts, demand continues or frequent drug treatment, which treatment, according to prior art methods of wound dressings, can be employed only on open wound. According to a preferred embodiment of the present invention the method may further comprise the step of incorporating at least one drug within the liquefied polymer, for delivery of the drug into the wound during or after generating the wound dressing. Hence the present invention provides solution to the problem of continues drug delivery, without the need to stripe off the wound dressing.

The process described hereinabove, ensures efficient manufacturing of nonwoven materials, which enjoy several mechanical and physical characteristics.

Hence, according to a preferred embodiment of the present invention, there is provided a nonwoven sterile wound dressing comprising at least one layer of polymer fibers shaped in accordance with an individual wound and body geometry. The wound dressing having various physical, mechanical and pharmacological, properties, which may be any combination of the following characteristics: (a) having a predetermined porosity; (b) flexible in accordance with a motion of the individual; (c) removable when placed under a sufficient amount of liquid; and (d) having at least one drug incorporated therein, for delivery of the drug into a body vasculature during or after application of the wound dressing.

It would be appreciated that when a skin defect is characterized by a large area of skin loss (such as in the case of a burn), the wound dressing may serve, at least temporarily, as an artificial skin, preventing exposure to infectious agents.

Besides being of utmost importance in numerous medical applications, device 20 and the method described above are useful in many other industrial applications. For example, the present invention can be employed for identification of individuals via fingerprints.

Thus, according to yet another aspect of the present invention there is provided a method of recording a fingerprint of a finger of an individual. The method comprising the steps of coating the finger by a nonwoven material and removing the nonwoven material from the finger so as to produce data information representative of the fingerprint of the finger.

As can be understood, the step of coating the finger is similar to the coating process detailed hereinabove, and it may be executed, for example, using device 20. Hence, once the coat is carefully removed from the finger a mirror image of the fingerprint is obtained on the inner surface of the coat. This mirror image may be processed in any method known in the art for the purpose of identifying the individual, constructing an appropriate data base or for any other purpose. In one example, the polymer fibers are manufactured with predetermined magnetic properties, so that the coat, once removed from the finger, may be used as an electronic identification device. Such a device may be used, e.g., as an "electronic key", which biometrically identifies a user by his fingerprint.

By a proper choice of the ingredients of the liquefied polymer, the present invention can also be used for adhering two objects. This can be done by more than one way. For example, if the objects to be joint are characterized by sufficient contact surface, the adhering is done by coating (employing the above described method) at least one contact surface and attaching the objects to one another. In this case the liquefied polymer is preferably selected to have dominant adhesive properties.

On the other hand, the two objects may be, for example, two blood vessels having open ends which need to be connected to one another during a surgery operation. In this case, the liquefied polymer is preferably selected to have dominant biological properties, such as, but not limited to, biocompatibility and/or biodegradability.

According to a preferred embodiment of the present invention the method of connecting the vessels comprises the steps of attaching the two open ends and, via electrospinning (using the method described above) providing a coat onto at least a portion of the two vessels so as to adhere the two open ends.

According to a preferred embodiment of the present invention, the liquefied polymer loaded into dispenser 22 may be, for example polyurethane, polyester, polyolefin, polymethylmethacrylate, polyvinyl aromatic, polyvinyl ester, polyamide, polyimide, polyether, polycarbonate, polyacrilonitrile, polyvinyl pyrrolidone, polyethylene oxide, poly (L-lactic acid), poly (lactide-CD-glycoside), polycaprolactone, polyphosphate ester, poly (glycolic acid), poly (DL-lactic acid), and some copolymers. Biolmolecules such as DNA, silk, chitozan and cellulose may also be used in mix with synthetic polymers. Improved charging of the polymer may also be required. Improved charging is effected according to the present invention by mixing the liquefied polymer with a charge control agent (e.g., a dipolar additive) to form, for example, a polymer-dipolar additive complex which apparently better interacts with ionized air molecules formed under the influence of the electric field. The charge control agent is typically added in the grams equivalent per liter range, say, in the range of from about 0.001 N to about 0.1 N, depending on the respective molecular weights of the polymer and the charge control agent used.

U.S. Pat. Nos. 5,726,107; 5,554,722; and 5,558,809 teach the use of charge control agents in combination with polycondensation processes in the production of electret fibers, which are fibers characterized in a permanent electric charge, using melt spinning and other processes devoid of the use of a precipitation electrode. A charge control agent is added in such a way that it is incorporated into the melted or partially melted fibers and remains incorporated therein to provide the fibers with electrostatic charge which is not dissipating for prolonged time periods, say weeks or months. In a preferred embodiment of the present invention, the charge control agent transiently binds to the outer surface of the fibers and therefore the charge dissipates shortly thereafter. This is because polycondensation is not exercised at all such that the chemical interaction between the agent and the polymer is absent, and further due to the low concentration of charge control agent employed. The resulting material is therefore, if so desired, substantially charge free.

Suitable charge control agents include, but are not limited to, mono- and poly-cyclic radicals that can bind to the polymer molecule via, for example, —C=C—, =C—SH— or —CO—NH— groups, including biscationic amides, phenol and uryl sulfide derivatives, metal complex compounds, triphenylmethanes, dimethylmidazole and ethoxytrimethylsians.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An electrospinning device for generating an electrospun polymer coat, said device comprising:
   (a) a dispenser for dispensing the liquefied polymer, and
   (b) a system of relocating electrodes;
   said dispenser and said system of relocating electrodes are at an effective potential difference providing a flow stream of dispensed polymer fibers along an axis through said dispenser to said system of relocating electrodes;
   wherein said dispenser and said system of relocating electrodes are accommodated in a tubular cavity axisymmetric to said stream axis;
   wherein said device further comprises a mechanism adapted for relocating said polymer fibers out of said cavity in a direction of said object of interest.

2. The electrospinning device of claim 1, wherein said cavity has a first terminal portion and a second terminal portion; said dispenser is disposed in said first terminal portion; said system of electrodes is disposed in said second cavity terminal portion.

3. The electrospinning device of claim 1, wherein said relocating mechanism comprises at least one blower, positioned adjacent to said dispenser, and generating airflow substantially directed along said axis.

4. The electrospinning device of claim 1, wherein said object is selected from the group consisting of an internal portion of a body of an organism, an external portion of a body of said organism, a skin of said organism, a wounded skin of said organism, an artery, a vein, and a rotating mandrel.

5. The electrospinning device of claim 1, wherein said dispenser comprises a mechanism for forming a jet of said liquefied polymer; said mechanism includes a dispensing electrode.

6. The electrospinning device of claim 1, further comprising a first reservoir for holding the liquefied polymer.

7. The electrospinning device of claim 1, further comprising a second reservoir for holding a pharmaceutical agent to be mixed with the liquefied polymer.

8. The electrospinning device of claim 1, further comprising a mechanism for intertwining at least a portion of said plurality of polymer fibers, said mechanism is adapted to provide at least one polymer fiber bundle moving along said longitudinal axis; said mechanism further comprises a system of intertwining electrodes, being laterally displaced from said dispenser, being at an intertwining potential relative to said dispenser and capable of providing an electric field having at least one rotating component about said axis.

9. The electrospinning device of claim 8, wherein said system of intertwining electrodes includes at least one rotating electrode, operable to rotate about said longitudinal axis.

10. The electrospinning device of claim 1, wherein said tubular cavity is characterized by a gradually decreasing cross-sectional area from said first cavity terminal portion to said second cavity terminal portion.

11. The electrospinning device of claim 1, wherein said first terminal is closed by a perforated plate positioned.

12. The electrospinning device of claim 1, wherein the liquefied polymer is biocompatible.

13. The electrospinning device of claim 1, wherein the liquefied polymer is selected from the group consisting of a biodegradable liquefied polymer and a biostable liquefied polymer.

14. The electrospinning device of claim 1, wherein the liquefied polymer is characterized by predetermined magnetic properties.

15. A method of generating an electrospun polymer coat on an object of interest, said method comprising
   (a) providing and electrospun device; said device comprising:
      i. a dispenser for dispensing the liquefied polymer, and
      ii. a system of relocating electrodes
   said dispenser and said system of relocating electrodes are at an effective potential difference providing a flow stream of dispensed polymer fibers along an axis through said dispenser to said system of relocating electrodes;
   said dispenser and said system of relocating electrodes are accommodated in a tubular cavity axisymmetric to said stream axis; said device further comprises a mechanism adapted for relocating said polymer fibers out of said cavity in a direction of said object of interest
   (b) dispensing the liquefied polymer along with relocating potential difference applied between a polymer dispenser and said system of relocating electrodes in a direction of an object so as to generate a coat onto said object
   wherein said step of dispensing said polymer is concurrently combined with a step relocating polymer fibers from a cavity accommodating said dispenser and said first system of electrodes by means of a relocating mechanism.

16. The method of claim 15, wherein said relocating is performed by generating airflow.

17. The method of claim 15, wherein said object is selected from the group consisting of an internal portion of a body of an organism, an external portion of a body of said organism, a skin of said organism, a wounded skin of said organism, an artery, a vein, and a rotating mandrel.

18. The method of claim 15, wherein said relocating potential difference is generated by said dispensing electrode and said system of relocating electrodes.

19. The method of claim 15, wherein said system of relocating electrodes comprises a circular electrode being at an relocating potential relative to said dispenser, and spaced apart from said dispenser, along said axis.

20. The method of claim 15, further comprising a step of intertwining at least a portion of said plurality of polymer fibers, so as to provide at least one polymer fiber bundle moving along said longitudinal axis.

21. The method of claim 15, wherein said step of intertwining is performed by a system of intertwining electrodes, being laterally displaced from said dispenser, being at an intertwining potential relative to said dispenser; said system of intertwining electrodes is adapted to provide said intertwining potential difference having at least one rotating component about said longitudinal axis.

22. The method of claim 15, further comprising incorporating at least one drug within said liquefied polymer, for delivery of said at least one drug into a vasculature of said organism, during or after generating the coat.

23. The method of claim 15, further comprising incorporating at least one drug within said liquefied polymer, for delivery of said at least one drug into said vessel during or after generating the coat.

24. The method of claim 15, wherein the liquefied polymer is biocompatible.

25. The method of claim 15, wherein the liquefied polymer is selected from the group consisting of a biodegradable liquefied polymer and a biostable liquefied polymer.

26. The method of claim 15, wherein said coat is a wound dressing; said wound dressing is electrospun in situ.

* * * * *